United States Patent [19]

Louvet-Plaisant et al.

[11] Patent Number: 5,891,903

[45] Date of Patent: Apr. 6, 1999

[54] USE OF MELATONIN IN A COMPOSITION FOR STABILIZING HYDROPHILIC GELLING POLYMERS

[75] Inventors: Nathalie Louvet-Plaisant, Chevilly Larue; Françoise Lebreton, Bures-Sur-Yvette, both of France

[73] Assignee: Societe L'Oreal S.A., Paris, France

[21] Appl. No.: 986,516

[22] Filed: Dec. 8, 1997

[30] Foreign Application Priority Data

Dec. 6, 1996 [FR] France ................................. 96 15045

[51] Int. Cl.⁶ .................................................. A61K 31/405
[52] U.S. Cl. .......................................................... 514/415
[58] Field of Search ............................................. 514/415

[56] References Cited

U.S. PATENT DOCUMENTS 5,688,520  11/1997  Karsenty et al. ....................... 424/434

FOREIGN PATENT DOCUMENTS 0438856  7/1991  European Pat. Off. .
0470385  3/1969  Switzerland .

*Primary Examiner*—Raymond Henley, III
*Attorney, Agent, or Firm*—Burns, Doane, Swecker & Mathis, L.L.P.

[57] ABSTRACT

The present invention relates to the use of melatonin or analogues thereof in a composition as an agent for stabilizing hydrophilic gelling polymers. The invention relates more particularly to cosmetic or pharmaceutical compositions for topical use.

14 Claims, No Drawings

USE OF MELATONIN IN A COMPOSITION FOR STABILIZING HYDROPHILIC GELLING POLYMERS

BACKGROUND OF THE INVENTION

Technical Field of the Invention

The present invention relates to the use of melatonin or analoges thereof for stabilizing compositions comprising hydrophilic gelling polymers, in particular in topical pharmaceutical or cosmetic compositions.

Hydrophilic gelling agents are very widely used in topical pharmaceutical or cosmetic compositions. These are, in particular, gelling agents such as polymers of natural and/or synthetic origin, among which mention may be made of carboxyvinyl polymers (carbomer), acrylic copolymers such as acrylate/alkyl acrylate copolymers, polyacrylamides or optionally modified polysaccharides such as hydroxypropyl cellulose.

It is known that these hydrophilic gelling polymers lose their viscosity under the effect of light, more particularly under the effect of UV radiation, and UVA and/or UVB screening agents are generally added to preparations containing them in order to overcome this problem. However, such screening agents are generally hydrophobic and are often considered to be responsible in intolerance phenomena such as photoallergy and/or phototoxicity, thus greatly limiting their use in topical pharmaceutical or cosmetic compositions.

The Applicant has found, surprisingly, that melatonin or analogues thereof can stabilize hydrophilic gelling polymers by preventing them from losing their viscosity under the action of light.

Melatonin, or N-acetyl-5-methoxytryptamine, which is secreted by the pineal gland, is especially known for its circadian activity in regulating the production of hormones, in particular for its influence on sleep rhythms.

It has also been described for its antioxidant activity and its use in dermocosmetology for improving the appearance of the skin (JP-A-61-221104; U.S. Pat. No. 4,746,674), or for protecting the skin against the effect of irradiation with UV rays (EP-A-0,438,856; E. Bangha & al., Dermatology 191, [2], 176, 1995).

Various topical compositions comprising melatonin for therapeutic or cosmetic use have been described, such as skincare lotions and skincare milks or creams (JP-A-61-221104). The article by Bangha et al., which relates to the efficacy of melatonin in eliminating UVB-induced erythema, also describes the use of melatonin in a nanocolloidal gel. Melatonin is always used as an active agent and its influence on the stability of hydrophilic gelling polymers has not been described or suggested in any document. It is also worth noting that melatonin is used in these compositions essentially for its antioxidant properties, in particular for capturing free radicals, although it is not a molecule screening in the solar spectrum, between 280 and 800 nm.

The present invention thus relates to the use of melatonin or at least an analogue thereof for stabilizing a composition comprising at least one hydrophilic gelling polymer. The term "stabilizing" is essentially understood to mean preventing their loss of viscosity under the action of light.

Among the melatonin analogues, mention may be made in particular of derivatives thereof, such as 5-methoxytryptamine, 5-methoxytryptophan, 5-methoxytryptophol, 5-methoxyindole-3-acetic acid and 6-hydroxymelatonin. Mention may also be made of melatoninergic agonists, such as those described in Patent Applications WO-A-95/17405, EP-A-0,447,285, EP-A-0,527,687, EP-A-0,530,087 and EP-A-0,591,057. These compounds may be of natural or synthetic origin.

Melatonin will preferably be used.

Among the hydrophilic gelling polymers, polymers of natural and/or synthetic origin are advantageously intended, among which mention may be made of carboxyvinyl polymers (carbomer), acrylic copolymers such as acrylate/alkyl acrylate copolymers, polyacrylamides or polysaccharides, such as guar gum, xanthan gum, or optionally modified celluloses, such as hydroxypropylcellulose.

The hydrophilic gelling polymer is preferably a carboxyvinyl polymer, for example marketed under the tradename Carbopol® by the company GOODRICH.

In accordance with the present invention, the use of melatonin or analogues thereof stabilizes cosmetic or pharmaceutical compositions, more particularly topical compositions comprising a hydrophilic gelling polymer as gelling agent. Topical compositions should contain a topically acceptable medium, that is to say compatible with the skin, the mucous membranes, the nails, the scalp and the hair.

The present invention also relates to a process for stabilizing a composition comprising at least one hydrophilic gelling polymer, by adding an sufficient amount of melatonin or at least an analogue thereof for preventing the loss of viscosity of the said polymer under the action of the light.

The weight ratio of the melatonin or analogues thereof to the hydrophilic gelling polymer is advantageously between 1/2000 and 20/1, preferably between 1/500 and 1/2.

Lastly, the present invention relates to cosmetic or pharmaceutical compositions, in particular topical compositions, comprising at least one hydrophilic gelling polymer and melatonin or at least an analogue thereof as an agent for stabilizing the said hydrophilic gelling polymer.

These compositions comprise between 0.001% and 0.2% by weight of melatonin or analogues thereof and between 0.01% and 3% by weight of hydrophilic gelling polymer. The weight percentage is expressed relative to the total weight of the composition.

The compositions containing melatonin or analogues thereof can be in any pharmaceutical form for topical use which is normally used, comprising at least one hydrophilic gelling agent, in particular in the form of an aqueous solution, emulsions of liquid or semi-liquid consistency of the milk type, or suspensions or emulsions of soft consistency of the cream or aqueous gel type. These compositions are prepared according to the usual methods of the art.

The amounts of the various usual constituents in the compositions are those used conventionally in the fields in question.

These compositions constitute in particular cleansing, protective, treatment or care creams for the face, for the hands, for the feet, for the major anatomical folds or for the body, (for example day creams, night creams, make-up-removing creams, foundation creams, sun-creams), liquid foundations, make-up-removing milks, protective or care body milks, sun-milks, skin care lotions, gels or mousses such as cleansing lotions, sun-lotions, self-tanning lotions, bath compositions, deodorizing compositions comprising a bactericidal agent, aftershave gels or lotions, hair-removing creams, insect-repellant compositions, pain-relief compositions and compositions for treating certain skin diseases such as eczema, acne rosacea, psoriasis, lichens and severe pruritus.

The cosmetic or dermatological composition can, in a known manner, also contain adjuvants that are common in the cosmetic or dermatological field, such as preserving agents, antioxidants, solvents, fragrances, fillers, screening agents, odour absorbers and dyestuffs. The amounts of these various adjuvants are those used conventionally in these fields, for example from 0.01% to 10% of the total weight of the composition.

The composition can contain hydrophilic active agents such as proteins or protein hydrolysates, amino acids, polyols, urea, allantoin, sugars and sugar derivatives, water-soluble vitamins, plant extracts and hydroxy acids, or active agents intended especially for preventing and/or treating skin complaints such as agents for modifying skin differentiation and/or proliferation and/or pigmentation, antibacterial agents, antiparasitic agents, antifungal agents, anti-inflammatory agents which may or may not be steroidal, antipruriginous agents, anti-free radical agents, antiseborrhoic agents such as progesterone, CGRP antagonists or substance P antagonists, or alternatively bradykinin antagonists, and antidandruff agents.

The examples below illustrate the present invention without, however limiting its scope. In these examples, percentages are expressed on a weight basis relative to the total weight of the compositions.

EXAMPLE 1

Carbomer marketed under the name
Carbopol 940 by the company GOODRICH 0.50%
Triethanolamine 0.50%
Melatonin 0.18%
Preserving agents qs
Dyes qs
Water qsp 100%

EXAMPLE 2

Glyceryl stearate 0.50%
Peg-100 stearate 2.00%
Cetyl alcohol 0.40%
Cyclomethicone 3.00%
Soybean oil 3.00%
Acrylates/$C_{10}$–$C_{30}$ alkyl acrylate
crosspolymer (CTFA) marked under the name
Carbopol 1382 by the company GOODRICH 0.30%
Melatonin 0.05%
Preserving agents qs
Water qsp 100%

EXAMPLE 3

Sodium laureth sulphate 2.00%
Glycerol 3.00%
Carbomer marketed under the name
Carbopol 940 by the company GOODRICH 0.20%
Carrageenan 0.30%
Sodium hydroxide 0.10%
Melatonin 0.03%
Preserving agents qs
Water qsp 100%
Stability Test:

Composition of example 1 comprising a hydrophilic gelling polymer and melatonin was exposed to UV radiation (wavelengths between 300 and 830 nm) in a closed Suntest CPS-Heraeus chamber, the samples being placed in naked glass bottles.

The viscosity of composition 1 was measured before exposure, after 4 hours' exposure and after 19 hours' exposure and compared with that of the same composition comprising no melatonin (Control). The measurements were taken using a Rheomat 108 E/R machine at a constant temperature (25° C.) and the reading was taken after 10 minutes of shearing with a No. 3 rotor and a No. 2 rotor.

The results obtained are given in the table below.

TABLE

| Viscosity | Control | Composition of example 1 |
|---|---|---|
| Before UV exposure | 37.5 Poises (M3) | 40 Poises (M3) |
| After 4 hours' exposure | 14 Poises (M3) (decrease in viscosity 62%) | 28 Poises (M3) (decrease in viscosity 30%) |
| After 19 hours' exposure | 2.5 Poises (M2) (decrease in viscosity 93%) | 16 poises (M3) (decrease in viscosity 60%) |

The above results show that melatonin stabilizes gelling polymers since a 60% decrease in viscosity after exposure for 19 hours is observed for composition 1 according to the invention, against only 4 hours of exposure for the melatonin-free control.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A cosmetic or pharmaceutical composition comprising at least one hydrophilic gelling polymer, and an amount of melatonin or an analog thereof effective to inhibit or prevent the loss of viscosity of said hydrophilic gelling polymer upon exposure of said composition to light, wherein the amount of said melatonin or analog thereof ranges from 0.001% to 0.2% by weight and the amount of said hydrophilic gelling polymer ranges from 0.01% to 3% by weight relative to the total weight of the composition.

2. The composition according to claim 1, wherein the melatonin analog is selected from the group consisting of 5-methoxytryptamine, 5-methoxytryptophan, 5-methoxytryptophol, 5-methoxyindole-3-acetic acid, 6-hydroxymelatonin, and their mixtures.

3. The composition according to claim 1, wherein the hydrophilic gelling polymer is selected from the group consisting of carboxyvinyl polymers (carbomer), acrylic copolymers, polyacrylamides, optionally modified polysaccharides, and their mixtures.

4. The composition of claim 3, wherein the polymer is a carboxyvinyl polymer.

5. The composition of claim 1, wherein the weight ratio of the melatonin or analog thereof to the hydrophilic gelling polymer ranges from 1/200 to 20/1.

6. The composition of claim 4, wherein the ratio of the melatonin or analog thereof to the hydrophilic gelling polymer ranges from 1/500 to 1/2.

7. A method for stabilizing a composition comprising at least one hydrophilic gelling polymer in order to prevent or inhibit the loss of viscosity of said polymer when said composition is exposed to light by adding to said composition a photostabilizing effective amount of at least one melatonin or melatonin analog.

8. The method according to claim 7, wherein the melatonin analog is selected from the group consisting of 5-methoxytryptamine, 5-methoxytryptophan, 5-methoxytryptophol, 5-methoxyindole-3-acetic acid, 6-hydroxymelatonin and their mixtures.

9. The method according to claim 7, wherein melatonin is used as the stabilizer.

10. The method according to claim 7, wherein the hydrophilic gelling polymer is selected from the group consisting of carboxyvinyl polymers (carbomer), acrylic copolymers, polyacrylamides, optionally modified polysaccharides and their mixtures.

11. The method according to claim 7, wherein the hydrophilic gelling polymer is a carboxyvinyl polymer.

12. The method according to claim 7, wherein the weight ratio of the melatonin or analogs thereof to the hydrophilic gelling polymer ranges from 1/2000 to 20/1.

13. The method according to claim 12, wherein said weight ratio ranges from 1/500 to 1/2.

14. The method according to claim 7, wherein the composition is a cosmetic or pharmaceutical composition.

* * * * *